United States Patent [19]

McDaniel, Jr. et al.

[11] Patent Number: 4,483,123
[45] Date of Patent: Nov. 20, 1984

[54] METHOD FOR MANUFACTURING AND PACKAGING A PET COLLAR

[75] Inventors: Joe D. McDaniel, Jr., Dallas; Paul L. Pruitt, Carrollton, both of Tex.

[73] Assignee: Zoecon Corporation, Palo Alto, Calif.

[21] Appl. No.: 407,006

[22] Filed: Aug. 10, 1982

Related U.S. Application Data

[62] Division of Ser. No. 206,916, Nov. 14, 1980, Pat. No. 4,348,321.

[51] Int. Cl.$^3$ .............................................. B65B 63/00
[52] U.S. Cl. ......................................... 53/428; 53/435
[58] Field of Search .................... 53/111 R, 122, 435, 53/479, 522, 428; 119/106; 424/27, 28, 29; 548/473, 478

[56] References Cited

U.S. PATENT DOCUMENTS

| | | | |
|---|---|---|---|
| 3,755,355 | 8/1973 | Kalbfeld | 548/478 |
| 3,849,439 | 11/1974 | Imamura et al. | 548/478 X |
| 3,904,746 | 9/1975 | Aries | 424/28 |
| 4,150,109 | 4/1979 | Dick et al. | 424/28 |
| 4,352,702 | 10/1982 | Bornstein | 53/479 |

*Primary Examiner*—Robert L. Spruill
*Assistant Examiner*—Steven P. Weihrouch
*Attorney, Agent, or Firm*—Donald W. Erickson; Jacqueline S. Larson; Hana Dolezalova

[57] ABSTRACT

A method for the manufacture of a packaged pet collar which includes preparing a blended composition of a vinylic resin, an ectoparasiticidally effective amount of recrystallized phosmet and a plasticizer, extruding the composition into a continuous length, cutting the extruded length into individual segments, affixing a buckle, and thereafter packaging the resultant pet collar in a pouch of spunbonded olefin. The packaged collar is characterized by the absence of offensive mercaptan type odor upon opening the package.

4 Claims, No Drawings

METHOD FOR MANUFACTURING AND PACKAGING A PET COLLAR

This is a division of application Ser. No. 206,916, filed Nov. 14, 1980, now U.S. Pat. No. 4,348,321.

This invention relates to an improved pet collar which provides effective and long-term control of ectoparasites of pets and to the method of manufacture.

Prior to the present invention, there has not been available a pet collar which provides effective and long-term control of the ectoparasites (fleas, ticks and mites) of pets. Pet collars now available which provide effective control for fleas and ticks suffer from one or more draw-backs. The pet collars now in use provide for control of fleas only or, in the case of a collar for both fleas and ticks, the period of effectiveness is up to five months.

The aforementioned problems of pet collars for the control of ectoparasites are overcome by the improved pet collar of the present invention. In addition to providing effective and long term control of both fleas and ticks, the pet collar of the present invention controls mite infestations that cause sarcoptic mange, a major problem for dogs. The pet collar of the present invention is prepared from a composition comprising a solid synthetic polymer such as a vinyl polymer and copolymers thereof, recrystallized phosmet and plasticizer.

Prior art pet collars for the control of ectoparasites are described by, for example, Aries et al., U.S. Pat. No. 3,814,061 (1974), Grubb & Baxter U.S. Pat. No. 3,852,416 (1974), Greenberg U.S. Pat. No. 3,918,407 (1975), Miller & Morales U.S. Pat. No. 3,944,662 (1976), Milionis & Spicer U.S. Pat. No. 4,041,151 (1977), Pasarela, U.S. Pat. No. 4,145,409 (1979), Greenberg and Cloyd U.S. Pat. No. 4,158,051 (1979), Dick and Romoi U.S. Pat. No. 4,150,109 (1979) and von Bittera et al., U.S. Pat. No. 4,225,578 (1980) and Aries, French Patent Publication No. 2,267,045 (1975). The Aries French Publication describes a large multitude of pesticides which are alleged to be useful in pet collars for the control of ectoparasites. Aries does not describe a composition for pet collars containing phosmet; however, in the multitude of possible ingredients within Aries description is included phosmet. In addition, Aries does not recognize the problem of offensive odor associated with a pet collar containing phosmet and does not suggest any solution to the problem.

The present invention provides a pet collar containing phosmet which overcomes the offensive odor associated with phosmet and method of manufacture thereof.

The pet collar of the present invention is characterized by being free of the offensive odor associated with phosmet, in addition, the pet collar of this invention is characterized by being essentially dry and having the property of providing a self-replenishing coating of particles of the active ingredient (phosmet) on the surface of the collar by migration of the active ingredient from the body of the collar, the migration occurring whenever particles of the active ingredient are displaced from the surface of the collar.

In preparation of the pet collar of the present invention, there can be employed any suitable solid synthetic polymer which is satisfactorily compatible with the plasticizer employed and recrystallized phosmet. The polymer needs to have adequate strength and flexibility to withstand shaping into a collar without cracking or crumbling and sufficient durability to withstand normal wear. Further, the resin must be one from which the plasticizer will not exude at normal temperatures and conditions, but, yet will permit adequate migration of the active ingredient from the body of the collar to the surface thereof. The foregoing requirements of the resin are fulfilled by solid vinylic resins, that is, a polymer form by polymerization through a vinylic double bond. Vinylic resins are typified by the polyvinyl halides, such as polyvinyl chloride, polyvinyl chloride-vinyl acetate and polyvinyl fluoride; the polyacrylate and polymethacrylate esters such as polymethyl acrylate and polymethyl methacrylate; and polyvinyl benzenes such as polystyrene and polyvinyl toluene. Preferably, the resin is a homopolymer or copolymer of vinyl chloride. The resin comprises from about 40% to 70%, usually from 45% to 65%, by weight of the total composition.

Plasticizers suitable for preparing the pet collar of the present invention are those conventionally employed in plasticizing solid vinylic polymers. The particular plasticizer or plasticizers employed will depend upon the polymer and its compatibility therewith. Suitable plasticizers include esters of phosphoric acid such as tricresyl phosphate, esters of phthalic acid such as dimethyl phthalate and dioctyl phthalate, and esters of adipic acid such as diisobutyl adipate. Other esters such as those of azelaic acid, maleic acid, rincinoleic acid, myristic acid, palmitic acid, oleic acid, sebacic acid, stearic acid and trimellitic acid as well as complex linear polyesters, polymeric plasticizers, and epoxidized soybean oils may be used. The plasticizer comprises from about 15% to 50%, usually 20% to 45%, by weight of the total composition.

The active ingredient, recrystallized phosmet, is included in an ectoparasiticidally effective amount, generally from 5% to 18%, by weight of the total composition.

Phosmet has the chemical name, 0,0-dimethyl S-phthalimidomethyl phosphorodithioate or N-(mercaptomethyl)-phthalimide S-(0,0-dimethyl) phosphorodithioate and is described by Fancher, U.S. Pat. No. 2,767,194 (1956). Commercial phosmet has an offensive odor. The odor is characterized as a mercaptan type odor. Following incorporation of phosmet into a resin collar, the odor, nevertheless, persists. U.S. Pat. No. 2,767,194 teaches purification of phosmet by crystallization from alcohol. Using alcohol, however, the offensive mercaptan odor is still present. In accordance with the present invention, technical phosmet is essentially free of mercaptan type odor by recrystallization of the technical phosmet from a mixture of hydrocarbon solvent and alcohol in the ratio of from about 1:2.5 to 1:1, respectively, by weight; preferably, from about 1:2 to 1:1. Preferably, the hydrocarbon solvent is an aromatic hydrocarbon such as toluene and the alcohol is methanol.

In the preferred embodiment, the recrystallization is repeated twice as described more fully in the examples. As used herein, the term "recrystallized phosmet" refers to phosmet obtained by the recrystallization of technical phosmet from a mixture of hydrocarbon solvent and alcohol.

In the manufacture of a pet collar of the present invention, a composition comprising vinylic resin, recrystallized phosmet and plasticizer is extruded or injection molded into the shape of a collar, buckle or similar fastening means affixed, and the collar sealed in a pouch made of a packaging material of fibrous, spunbonded olefin. A suitable fibrous spunbonded olefin is spunbonded polyethylene. Preferably, the spunbonded olefin is a high density polyethylene providing a packaging material having a thickness of about 5 to 10 mils and a basis weight of about 40 to 110 grams per square meter. An example of the preferred fibrous, spunbonded olefin packaging material is a high density polyethylene manufactured by E. I. DuPont De Nemours & Co., Wilmington, Del. under the trademark Tyvek, for example, Tyvek type 10. The use of a spunbonded olefin as the packaging material results in a collar of the present invention which is free of offensive odor upon receipt and opening of the packaged collar by the user. The use of materials such as foil, saran, polyethylene coated paper and nylon laminate conventionally used as packaging materials resulted in packaged collars which on opening yielded an offensive mercaptan type odor.

Other ingredients such as stabilizers, lubricants, fillers, deodorants, perfumes and coloring materials can be included in the compositions for preparing the pet collar of the present invention without changing the fundamental properties thereof. Suitable stabilizers are the antioxidants and agents which protect the resin from ultraviolet radiation and undue degradation during processing such as extrusion, a wide variety of which are commercially available. Some stabilizers such as epoxidized soybean oils serve also as a secondary plasticizer. Stearates including stearic acid and low molecular weight polyethylene are examples of lubricants which can be used. These ingredients may be used in a concentration of up to about 20% by weight of the total composition.

Within a short time after processing, fine particles or crystals of phosmet migrate from within the body of the collar and form a coating of particles or crystals, resembling a dust or powder, on the surface of the collar. As the particles of phosmet are displaced or shaken from the surface of the collar due to the normal activity of the animal, additional particles appear by migration from the body of the collar to replace particles displaced from the surface—i.e., the displaced particles are replenished continuously. The normal movement of the animal results in phosmet crystals being distributed substantially over the entire coat of the animal and effecting its ectoparasiticidal activity over a large part of the animal's body. Fleas and ticks are controlled by the collars of the present invention for up to about one year.

As used herein, the term "pet" means a dog or cat.

The following examples are provided to illustrate the practice of the present invention. Parts are by weight. Temperature is degrees centigrade unless otherwise specified.

EXAMPLE 1

To a glass lined vessel equipped with agitator and condenser is added 216 parts toluene and 197 parts methanol followed by 500 parts technical phosmet, with agitation. The mixture is heated, with continuous agitation, until the phosmet dissolves and then heated at reflux (64°) for about 30 minutes. The solution is cooled to about 0° to 5°, seeded with phosmet crystals if necessary, and then, with continuous agitation, maintained at about 0° to 5° for about one hour. The mixture is then filtered using a Furan filter and saving the mother liquor for reuse. The vessel is rinsed with 270 parts cold methanol (5°) and precipitate washed with the cold methanol. The precipitate is collected and added to mixture of toluene (209 parts) and methanol (190 parts). The mixture is agitated and heated at reflux for about 30 minutes and then cooled to 0° to 5°. After about one hour, the mixture is filtered and washed as above, air dried and then dried for about 18 hours at 20° to 30° to yield recrystallized phosmet, m.p. 70°–72°, white to slightly off-white crystals with no mercaptan type odor.

Technical phosmet is manufactured by the Stauffer Chemical Company.

EXAMPLE 2

A mixture of 150 ml of toluene, 150 ml. of methanol and 300 g. of technical phosmet is heated in a hot-water bath until homogenous. The solution is poured into Buchner funnel with suction flask. The flask is agitated vigorously in ice water bath until all crystals formed. Liquid is poured off and filtered through Buchner funnel with suction, rinsing with cold methanol (20 ml). The crystals are dried at 55° for one hour. Color of technical phosmet (pinkish) changed to white to slightly off-white and only very faint mercaptan type odor remained. The foregoing procedure is repeated and the crystals, air dried, had no detectable mercaptan type odor. Purity 98% and mositure less than 2% water.

The use of methanol alone as the solvent improved the color but did not remove the mercaptan type odor. The use of toluene and methanol in the ratio of 1:3, respectively, in the above procedure, changed the color of technical phosmet to off-white but, the mercaptan type odor remained.

The above procedure was repeated using 1.0 kg. of technical phosmet, 0.5 liter of toluene and 1.0 liter of methanol yielding recrystallized phosmet, white to slightly off-white, having no mercaptan type odor.

EXAMPLE 3

Polyvinyl chloride (49.4 parts) is mixed in a high intensity mixer (Henschel) at 3600 rpm until the polymer reaches about 140° F. To the polymer is added epoxidized oil (2.3 parts), bis(2-ethylhexyl) terephthalate (29.5 parts) and stabilizer (0.8 parts) with mixing, 135°–155° F. Recrystallized phosmet (17.3 parts) is added and mixed until a homogeneous dry blend is obtained. To the blend, with mixing, is added titanium dioxide pigment (0.5 part) followed by stearic acid (0.2 part). The blend is then cooled to about 90° F.

The polyvinyl chloride is a high molecular weight polyvinyl chloride homopolymer under the name Diamond 550 by the Diamond Shamrock Corporation.

Epoxidized oil is 2-ethylhexyl epoxytallate known as Drapex 4.4 from the Argus Chemical Company.

Stabilizer is Mark 1500, phosphite stabilizer, of Argus Chemical Company.

Titanium dioxide is white pigment known as PMS 355-T by Plastic Molders Supply, Ft. Worth, Tex.

EXAMPLE 4

The blend prepared in Example 3, is extruded using a single stage screw with a screw temperature of 320° F., die temperature of 330° F. and backpressure of about 300 psi. The extrudate, 0.563 inches wide and 0.130 inches thick, is cooled by running through a water bath and then dried using a compressed air drier tube. The extrudate is then cut into segments of 22 inches, a buckle added by a steel rivet and the resulting collar rolled or coiled. The rolled collar is then packaged in a pouch made by placing the rolled collar between two sheets of spunbonded olefin measuring 4.5 by 5.5 inches each and sealing the four sides. The sealing of the spunbonded olefin to form the pouch is accomplished using impulse sealing to seal the material to itself or using thermoplastic resin adhesive. The pouch is free from punctures and slits and is completely sealed. The spunbonded olefin used in the foregoing is a high density polyethylene under the name Tyvek 1073D by E. I. DuPont De Nemours & Co. (Inc.).

Pet collars of the present invention manufactured by the foregoing method do not have the offensive mercaptan type odor when manufactured or after storage, including storage in the sealed spunbonded olefin pouches, of several months at room temperature. In comparison, collars of the present invention when made as above with the exception of sealing in a pouch made of conventional packaging material such as paper/foil laminate emit an offensive mercaptan type odor upon opening the pouch after storage for only one month at room temperature or below (50° F.).

Collars made in accordance with Examples 3 and 4 were fitted on dogs for testing against the American Dog Tick (*Dermacentor varabilis*), Brown Dog Tick (*Rhipicaphalus sanguineus*), and fleas (Centocephalus sp.). The collars were found to provide effective control of both ticks and fleas after ten months. The collars were not irritating to the dogs throughout the test.

What is claimed is:

1. A method for the manufacture of a packaged, flexible, solid, ectoparasiticidally effective pet collar which comprises the steps of:
    (a) preparing a thorough blend of a solid composition comprising a solid, vinylic resin, ectoparasiticidally effective amount of recrystallized phosmet and plasticizer; said recrystallized phosmet having been prepared by recrystallization of phosmet in a toluene and methanol mixture in which the ratio of toluene and methanol is within 1:2.5 to 1:1 by weight, and being free of offensive mercaptan type odor;
    (b) extruding said composition to form a continuous length of extrudate having a width and thickness suitable for a pet collar;
    (c) cutting said extrudate into individual segments suitable for a pet collar and affixing a buckle at one end of the segment; and
    (d) sealing each segment in a pouch made of spunbonded olefin, said packaged collar characterized by the absence of offensive mercaptan type odor upon opening of the package.

2. The method according to claim 1 wherein the resin is a homopolymer or copolymer of vinyl chloride and the spunbonded olefin is high density polyethylene.

3. The method according to claim 2 wherein the resin is polyvinyl chloride.

4. The method according to claim 2 wherein the spunbonded olefin has a thickness of about 5 to 10 mils and a weight of about 40 to 110 grams per square meter.

* * * * *